(12) United States Patent
Urushihata et al.

(10) Patent No.: US 8,641,611 B2
(45) Date of Patent: Feb. 4, 2014

(54) DISEASE DIAGNOSTIC SYSTEM

(75) Inventors: Naoki Urushihata, Chiyoda-ku (JP);
Hideki Tanemura, Chiyoda-ku (JP);
Yukinobu Tajima, Chiyoda-ku (JP);
Syuji Hirohama, Chiyoda-ku (JP)

(73) Assignee: Seems Inc., Tokyo (JP)

( * ) Notice: Subject to any disclaimer, the term of this patent is extended or adjusted under 35 U.S.C. 154(b) by 1341 days.

(21) Appl. No.: 11/666,283

(22) PCT Filed: Oct. 26, 2005

(86) PCT No.: PCT/JP2005/019662
§ 371 (c)(1),
(2), (4) Date: Apr. 25, 2007

(87) PCT Pub. No.: WO2006/046588
PCT Pub. Date: May 4, 2006

(65) Prior Publication Data
US 2008/0091085 A1    Apr. 17, 2008

(30) Foreign Application Priority Data
Oct. 28, 2004   (JP) ................................. 2004-313663

(51) Int. Cl.
*A61B 5/00*   (2006.01)
(52) U.S. Cl.
USPC ........................................................ 600/300
(58) Field of Classification Search
USPC ............ 600/300, 301, 529; 128/903–905, 920
See application file for complete search history.

(56) References Cited

U.S. PATENT DOCUMENTS 4,772,559 A * 9/1988 Preti et al. ....................... 436/64
4,884,435 A * 12/1989 Ehara ............................ 73/23.34
5,996,586 A * 12/1999 Phillips ........................... 128/898
6,180,414 B1 * 1/2001 Katzman ........................ 436/181
6,221,026 B1 * 4/2001 Phillips ........................... 600/532

(Continued)

FOREIGN PATENT DOCUMENTS

EP  0 317 299   5/1989
JP  1-131444    5/1989

(Continued)

OTHER PUBLICATIONS

An Artificial Olfactory system based on gas sensor array and back-progagation neural network, F. Yin, J. Wang, and C. Guo (Eds.): ISNN 2004, LNCS 3174, pp. 892-897, 2004.*

(Continued)

*Primary Examiner* — Bill Thomson
*Assistant Examiner* — Davin K Sands
(74) *Attorney, Agent, or Firm* — Kratz, Quintos & Hanson, LLP

(57) ABSTRACT

[Problem]
To provide a disease diagnostic system capable of diagnosing with high accuracy whether a subject is afflicted with a disease, without inflicting pain on the subject.
[Means for Resolution]
The disease diagnostic system includes collecting means (5) for collecting a substance (e.g., aspiration, sweat, human waste or urine) emitting an odor (e.g., mouth odor, body odor or underarm odor) and storing the same therein, measuring means (10) for measuring whether an indicated substance indicative of the existence of a disease is contained in the odor-emitting substance stored in the collecting means (5), and control means (20) for processing a signal indicative of a result of measurement by the measuring means (10) to determine whether the subject (2) is being afflicted with a disease.

2 Claims, 11 Drawing Sheets

(56) References Cited

U.S. PATENT DOCUMENTS

| | | | |
|---|---|---|---|
| 6,244,096 B1 | 6/2001 | Lewis et al. | 73/23.2 |
| 6,341,232 B1* | 1/2002 | Conn et al. | 604/20 |
| 6,461,306 B1 | 10/2002 | Hanson, III | 600/532 |
| 6,468,222 B1* | 10/2002 | Mault et al. | 600/531 |
| 6,491,647 B1* | 12/2002 | Bridger et al. | 600/585 |
| 6,540,691 B1* | 4/2003 | Phillips | 600/532 |
| 6,598,459 B1* | 7/2003 | Fu | 73/23.34 |
| 6,631,333 B1* | 10/2003 | Lewis et al. | 702/24 |
| 6,712,770 B2* | 3/2004 | Lin et al. | 600/532 |
| 7,081,095 B2* | 7/2006 | Lynn et al. | 600/538 |
| 2002/0059030 A1* | 5/2002 | Otworth et al. | 702/19 |
| 2003/0008407 A1* | 1/2003 | Fu | 436/161 |
| 2003/0060726 A1 | 3/2003 | Lin et al. | 600/532 |
| 2003/0092186 A1* | 5/2003 | Pressman et al. | 436/46 |
| 2003/0143750 A1 | 7/2003 | Shih et al. | 436/113 |
| 2003/0172717 A1* | 9/2003 | Kita et al. | 73/23.34 |
| 2003/0219768 A1* | 11/2003 | Beebe et al. | 435/6 |
| 2004/0053322 A1* | 3/2004 | McDevitt et al. | 435/7.1 |
| 2004/0100376 A1* | 5/2004 | Lye et al. | 340/539.12 |
| 2004/0122702 A1* | 6/2004 | Sabol et al. | 705/2 |
| 2004/0122707 A1* | 6/2004 | Sabol et al. | 705/2 |
| 2004/0135684 A1* | 7/2004 | Steinthal et al. | 340/522 |
| 2005/0085740 A1* | 4/2005 | Davis et al. | 600/532 |
| 2005/0177057 A1* | 8/2005 | Friedman et al. | 600/543 |
| 2006/0073483 A1* | 4/2006 | White et al. | 435/6 |
| 2008/0077331 A1* | 3/2008 | Lewis et al. | 702/30 |

FOREIGN PATENT DOCUMENTS

| | | |
|---|---|---|
| JP | 2002-534697 | 10/2002 |
| JP | 2003-79601 | 3/2003 |
| JP | 2004-108861 | 4/2004 |
| JP | 2004-527299 | 9/2004 |
| WO | WO 96/12949 | 5/1996 |
| WO | WO 01/13087 | 2/2001 |
| WO | WO 01/63277 | 8/2001 |
| WO | WO 02/080778 | 10/2002 |

OTHER PUBLICATIONS

Extended European Search Report issued on a counterpart application mailed Jul. 14, 2011 (4 pages).

* cited by examiner

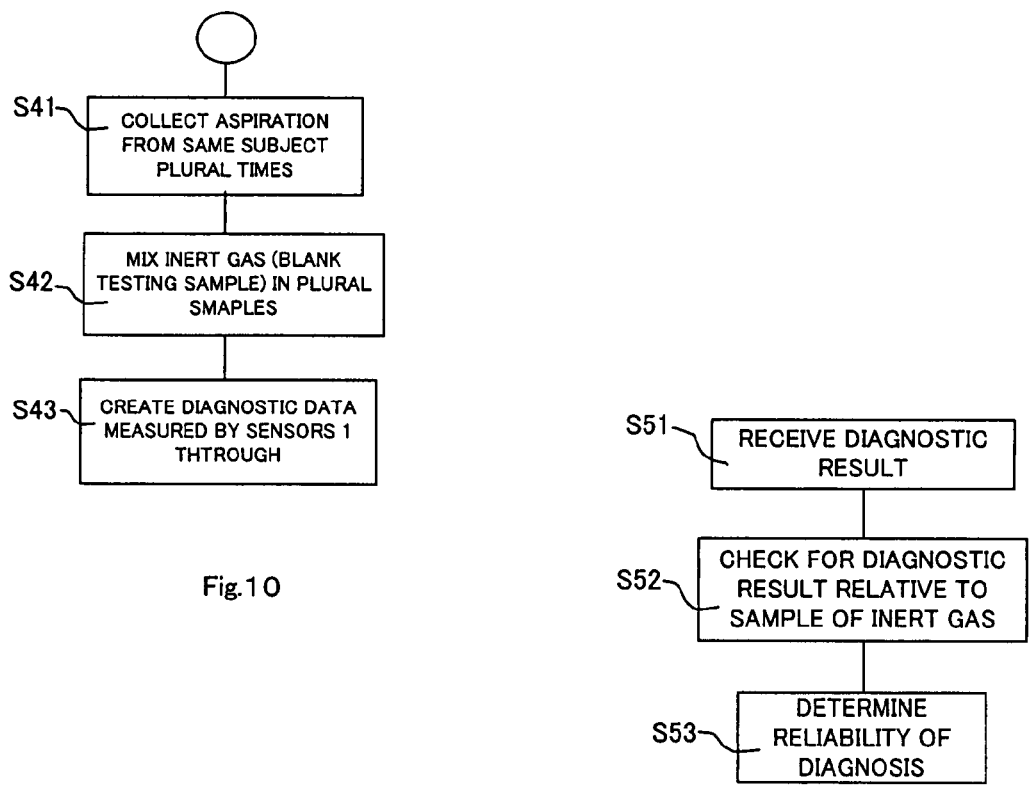
Fig.10
Fig.11
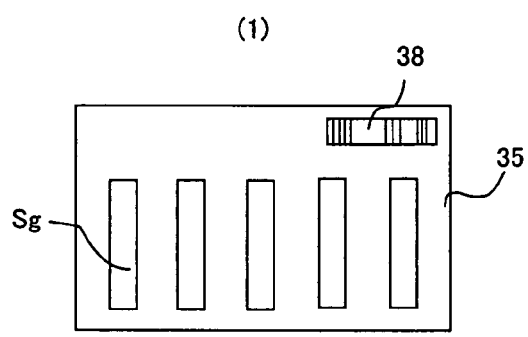
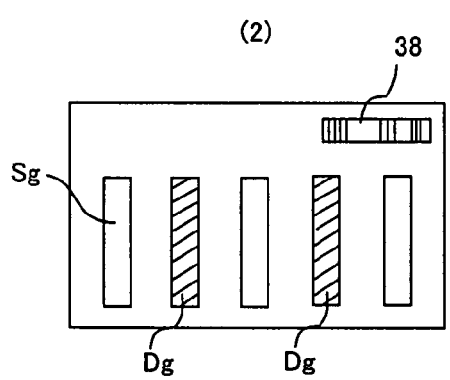
Fig.12

DISEASE DIAGNOSTIC SYSTEM

TECHNICAL FIELD

The present invention relates to a disease diagnostic system capable of diagnosing with predetermined accuracy or higher and easily whether a subject is being afflicted with a disease.

BACKGROUND ART

There appears to be a trend to have put the brake on an increase in the number of smokers through the years. However, the disease rate of lung cancer and the death toll due to the lung cancer are still maintained at high numerical values. For instance, the medical institution of US estimates that the rate of incidence of the lung cancer will increase.

This is considered to occur due to, for example, the problem of asbestos or the like and such environmental factors as to increase the rate of lung cancer incidence.

There has been an extremely strong demand for early detection of diseases, particularly, lung cancer under such conditions. Various techniques have been developed even in relation to the diagnosis of lung cancer.

If part of lung tissue is detected from within the body of a subject and the lung tissue is analyzed pathologically, it is then possible to determine the presence or absence of affection with lung cancer with high accuracy. It is however necessary to make an incision in body surface portion of the subject for the purpose of taking out the tissue to be analyzed from within the body of the subject. This puts an enormous load on the subject.

Therefore, there has been a demand for determination of the presence or absence of a disease, particularly, lung cancer without making an incision in the tissue of the body of the subject as much as possible, in other words, by an non-incision method.

To meet such a demand, there has been provided, for example, a technique for administering fluorescent target-oriented structure having biocompatibility specifically taken in due to tumor tissues to a subject, projecting excitation light having wavelengths ranging from 401 nm to about 500 nm onto the subject and observing fluorescence emitted by irradiation of the target-oriented structure to thereby determine the presence or absence of cancer tissues (refer to a patent document 1).

According to the above prior art, however, there is a need to administer the fluorescent target-oriented structure to the subject. There exists the subject that feels extreme anguish against such administration.

As a method for diagnosing lung cancer by a non-incision method other than the above, there exists a technique for analyzing and determining various body fluids, secretions or excrements as an alternative to the detection of the body tissues by the incision of the body surface portion. Upon handling of the body fluids, secretions or excrements, however, a large amount of labor is required to achieve the diffusion into an ambient environment. Further, there also exists a case in which each subject feels emotional distress and physical pain against the submission of such body fluids, secretions or excrements to doctors or the like corresponding to others.

Although various ones have been proposed as methods for diagnosing diseases, particularly, lung cancer even in addition to above, they present problems in terms of the accuracy of diagnosis.

Patent document 1: Japanese Patent Laid-Open No. 2004-527299

DISCLOSURE OF THE INVENTION

Problems to be Solved by the Invention

The present invention has been proposed in view of the above prior art. It is an object of the present invention to provide a disease diagnostic system capable of diagnosing with high accuracy whether a subject is afflicted with a disease, without inflicting pain on the subject.

Means for Solving the Problems

As a result of various studies, the present inventors have found out that odors peculiar to an afflicted disease exist in, for example, exhalation or aspiration of a subject high in the potentiality of being subjected to the disease. For instance, the aspiration of the subject high in the potentiality of lung cancer is different from aspiration of a subject low in its potentiality and contains aniline and/or ortho-toluidine. Further, the present inventors have focused on the point that if the aspiration is simply determined, then a burden on the subject is far lightened as compared with the case in which the fluorescent target-oriented structure is administered thereto, and if it is determined whether aniline and/or ortho-toluidine is contained in the aspiration, it is then possible to determine with high accuracy whether the subject is being afflicted with the lung cancer.

A disease diagnostic system of the present invention has been created based on the above findings. The disease diagnostic system includes collecting means (5) for collecting a substance (e.g., aspiration, sweat, human waste or urine) emitting an odor (e.g., mouth odor, body odor or underarm odor) and storing the same therein, measuring means (10) for measuring whether an indicated substance indicative of the existence of a disease is contained in the odor-emitting substance stored in the collecting means (5), and control means (20) for processing a signal indicative of a result of measurement by the measuring means (10) to determine whether the subject (2) is being afflicted with a disease.

If, for example, the disease to be detected is of lung cancer, the "odor-emitting substance" collected from the subject (2) is of aspiration (Ax) of the subject, and the indicated substance is aniline, then the above disease diagnostic system has collecting means (5) for collecting and storing the aspiration (Ax) of the subject (2), measuring means (sensor 10) for measuring whether aniline is contained in the aspiration (Ax) stored in the collecting means (5), and control means (20) for processing a signal indicative of the result of measurement by the measuring means (10) to determine whether the subject (2) is being afflicted with the lung cancer.

Here, a sensitivity portion of the measuring means (10) may preferably be constituted of a substance (e.g., aniline hydroxylase) corresponding to enzyme extremely high in the selectivity of reaction with aniline.

If the disease to be detected is of lung cancer and the indicated substance is ortho-toluidine, then a lung cancer diagnostic system of the present invention has collecting means (5) for collecting and storing aspiration (Ax) of a subject (2), measuring means (sensor 10) for measuring whether ortho-toluidine is contained in the aspiration (Ax) stored in the collecting means (5), and control means (20) for processing a signal indicative of the result of measurement by the measuring means (10) to determine whether the subject (2) is being afflicted with the lung cancer.

In the present invention, the measuring means (10) is provided in the form of plural types (e.g., four types or eight types of sensors). The control means (20) may preferably be constructed so as to perform processing for setting axial lines extending radially in arbitrary directions with an origin as a center on the same plane by the same number as the types of the measuring means (10) (thereby setting a so-called "radar chart"), associating the respective axial lines with the plural types of measuring means (10) in a 1:1 relationship arbitrarily, plotting the results of measurement by the measuring means (10) on the associated axial lines (thereby creating a graphic form on the radar chart), and determining according to each (graphic form CR created on the radar chart) of graphic forms defined by plural plots whether an indicated substance (e.g., aniline or ortho-toluidine) indicative of the existence of a disease exists.

Here, when it is determined according to the shape of the graphic form (graphic form CR created on the radar chart) whether the indicated substance indicative of the existence of the disease exists, a pattern recognition technique and conventionally-known various technique for determining similarities of other graphic forms can be applied.

Alternatively, in the present invention, the measuring means (10) may preferably be constructed to be capable of sensing only an indicated substance showing the existence of a disease to be detected and detecting the concentration of the indicated substance.

That is, the present invention is capable of using not only the sensor constructed by combining the plural sensors but also, for example, a sensor (sensor that reacts to an indicated substance (e.g., aniline, ortho-toluidine or the like) in a so-called "1:1" relationship) that reacts to only an odor indicative of lung cancer or other disease to be detected or the indicated substance and detects it, e.g. a thin film sensor (3).

Here, the thin film sensor is constituted of a porous material (e.g., organic polymer) in which a large number of pores formed in a nano-level are formed. There can be used one that exhibits or exerts selectivity necessary as the sensor by intruding molecules of a substance to be detected in the pores formed in the nano-level. By changing the formed modes or patterns of pores in various ways, extremely high selectivity, i.e., the property of sensing only an indicated substance to be detected can be obtained.

In addition to above, the thin film sensor can be constructed so as to be capable of detecting even the concentration of a detected target (an indicated substance indicative of the existence of a disease to be detected) together because an output signal is transmitted in association with the amount of the detected target intruded in the pores.

Further, the thin film sensor is preferably constructed to be capable of being used even in the air (within a vapor phase environment) and in the liquid (within a liquid phase environment).

Incidentally, the sensor may be constituted of a semiconductor (e.g., metal oxide semiconductor) or an optical sensor may be used.

The present invention is preferably constructed in such a manner that the collecting means (5) and the measuring means (10) are provided in the same place, whereas the control means (20) is provided in a place (central analysis center) (20) spaced away from the collecting means (5) and the measuring means (10), and the collecting means (5) and the measuring means (10), and the control means (20) are connected to one another by an information network (40) (they are connected to one another electronically or on an information processing basis by the information network), and a signal indicative of a result of measurement by each measuring means (10) is transmitted to the control means (40) via the information network.

Here, the present invention is preferably constructed in such a manner that an analysis device (like gaschromatography, for example) is disposed in the place where the control means is provided, and each sample per se of aspiration collected from a subject is forwarded or transported to the corresponding place or spot as needed (by transport means such as a car, a train or the like).

Preferably, an identification code corresponding to the subject is combined with a result-of-measurement signal upon transmission of the signal indicative of the result of measurement by the measuring means to the control means via the information network, and the combined signal is transmitted to the control means via the information network.

Further, the Internet, the local area network (LAN) and other various circuit networks can be applied as the information network.

Upon implementation of the present invention, preferably, a plurality of samples of collected aspiration are prepared for the same subject, and an inert gas is used for arbitrary samples of the plural samples (in other words, a blank test is effected thereon).

In the present invention, the diseases to be detected such as the lung cancer and others include not only the lung cancer but also other cancers and various diseases.

As an indicated substance corresponding to each of substances (e.g., aspiration, sweat, human waste and urine) emitting odors (e.g., mouth odor, body odor and underarm odor) indicative of cancers and other various diseases, any one of substances is chosen which is selected from alkane, alkene, alkine, diene, cyclic carbon hydride, aliphatic carbon hydride, acyclic carbon hydride, arene, alcohol, ether, ketone, aldehyde, carbonyl, carbanion, polynuclear aromatic compounds, biological molecules, isoprene, isoprenoid, protein, volatile organic compounds (VOC), VOA, indole, skatole, diamine, pyridine, picoline, sulphuric compounds, halogenated compounds, fatty acid, organic acid, organic base, non-volatile gas, CO, $CO_2$, NO, $NO_2$, $NH_3$, $H_2$, S, and COS, or aniline and ortho-toluidine referred to above.

Effects of the Invention

According to the present invention equipped with the above construction, since aspiration of a subject may be collected, there is no need to make an incision in the body surface of the subject and administer a special substance to the subject. It is also unnecessary to put a load on the subject physically and/or mentally. If, for example the disease is of lung cancer, then a decision as to whether the subject is being afflicted with the lung cancer can be made with high accuracy by determining whether aniline and/or ortho-toluidine is contained in the aspiration.

If the present invention is constructed so as to perform processing for setting axial lines extending radially in arbitrary directions with an origin as a center on the same plane by the same number as the types of the measuring means (thereby setting a so-called "radar chart"), associating the respective axial lines with plural types of measuring means in a 1:1 relationship arbitrarily, plotting the results of measurement by the measuring means on the associated axial lines (thereby creating each of graphic forms on the radar chart), and determining according to each (the graphic form created on the radar chart) of the graphic forms defined by plural plots whether aniline and/or ortho-toluidine exists if the disease is of, for example, lung cancer, it is possible to determine whether aniline and/or ortho-toluidine exists in aspiration of a subject, using plural types of sensors unsatisfactory in the reaction selectivity to aniline and/or ortho-toluidine even when it is not possible to prepare measuring means satisfactory in the reaction selectivity to aniline and/or ortho-toluidine.

Thus, if the disease is of lung cancer, for example, then a high accuracy decision can easily be carried out using sensors which are not satisfactory in the reaction selectivity to aniline and/or ortho-toluidine but easy to operate and come to hand.

In the present invention, if the measuring means is constituted of a thin film sensor capable of sensing only the concentration of an indicated substance showing the existence of a disease, to be detected and detecting the concentration of the indicated substance, then only the indicated substance to be detected can be sensed and the concentration of the corresponding indicated substance can also be detected along with it.

If the present invention is constructed in such a manner that collecting means and measuring means are provided in the same place, whereas control means is provided in a place spaced away from the collecting means and the measuring means, and the collecting means and the measuring means, and the control means are connected to one another by an information network, and a signal indicative of a result of measurement by each measuring means is transmitted to the control means via the information network, then the subject side may prepare only the aspiration collecting means and measuring means relatively easy to come to hand and operate.

Thus, it is possible to carry out with ease and high accuracy via an information network, a diagnosis of whether solitary old people or the like living in isolated islands, medically underserved villages and cities are afflicted with lung cancer. As a result, contributions to thank and welfare fields can be expected.

If upon implementation of the present invention, it is constructed in such a manner that a plurality of samples of collected aspiration are prepared for the same subject and an inert gas is used for arbitrary samples of the plural samples (in other words, a blank test is effected thereon), it is possible to estimate according to how data on the blank test is determined, whether mistakes exist in the handling or the like of data or samples in the presence of a subject and check for reliability of each individual or institution that has carried out the collection of each sample and data processing.

BEST MODE FOR CARRYING OUT THE INVENTION

Preferred embodiments of the present invention will hereinafter be described with reference to the accompanying drawings.

FIGS. 1 and 2 show a first embodiment of the present invention.

As described above, aniline or ortho-toluidine is contained in the expiratory air or aspiration Ax of the subject 2 high in lung-cancer potential. In the first embodiment, a sensor that selectively reacts to aniline and/or ortho-toluidine is used to determine whether aniline and/or ortho-toluidine is contained in the aspiration Ax of the subject 2 a predetermined value (threshold value or more) or more. When aniline and/or ortho-toluidine is contained in the aspiration Ax, it is judged that the potentiality of lung cancer can occur.

In FIG. 1 showing a system construction of the first embodiment in block form, a sensor 10 that selectively reacts to aniline and/or ortho-toluidine of the aspiration Ax is provided in a case or box-like acquisition means 5 for acquiring or collecting the aspiration Ax of the subject 2 and connected to an amplifier 12 by means of a signal line L10.

As the acquisition means for the aspiration Ax, known and commercially-available various devices can be applied as they are.

As the sensor 10, for example, a sensor is used in which aniline hydroxylase corresponding to enzyme that selectively reacts to aniline is placed in a sensitivity portion. The sensor 10 may be a known one which detects a change in current or voltage. Alternatively, the above-described thin film sensor is used as the sensor 10.

As is generally known, the amplifier 12 has the function of amplifying a signal detected based on a small current or voltage and is configured so as to facilitate subsequent computing processing. The amplifier 12 is connected to an A/D converter 14 by a signal line L12.

The A/D converter 14 is configured so as to digitize the amplified analog signal sent from the sensor 10 and has the function of outputting the signal in a data format adapted to a control means 20.

The control means 20 comprises an interface 22 which receives the digital signal sent from the A/D converter 14, a comparing means 26, a data memory or storage device (database) 24 and a determining means 28. These devices are configured so as to process digital data.

The interface 22 has code adaptation and other functions in such a manner that the digital signal supplied from the A/D converter 14 can be processed by the control means 20. The interface 22 is connected to the comparing means 26 by a signal line L22.

The data memory device 24 has the function of storing a large amount of past data about subjects therein, storing therein a threshold value corresponding to a numerical value defined as the boundary indicative of whether the corresponding subject has the potentiality of lung cancer and transmitting the data and/or threshold value as needed. And the data memory device 24 is connected to the comparing means 26 by a signal line L24.

Now, the threshold value is determined according to the sex, age, height and weight of a subject, a past history thereof and other various physical conditions. The threshold value is not necessarily limited to a signal numeric value. Such a threshold value is determined case by case by the accumulation of diagnostic data.

The comparing means 26 has the function of comparing data detected by the sensor 10 from the aspiration Ax of the subject 2 and processed thereby with the past data stored in the data memory device 24. The comparing means 26 is connected to the determining means 28 by a signal line L26.

The determining means 28 has the function of receiving the result of comparison by the comparing means 26 and determining the potentiality of lung cancer relative to the aspiration Ax of the subject 2. When, for example, the result of measurement exceeds the threshold value and an aniline and/or ortho-toluidine content lying in the aspiration Ax of the subject 2 is high, the determining means 28 determines that "there is high potential for lung cancer". The result of determination by the determining means 28 is transmitted to a display unit 30 by a signal line L28.

Operations of the first embodiment equipped with the above construction will be explained with reference to even a flowchart shown in FIG. 2.

In FIG. 2, aspiration Ax of the subject 2 is first collected by the acquisition means 5 (Step S1).

Next, the aspiration Ax is measured by the sensor 10 which selectively reacts to aniline and/or ortho-toluidine (Step S2). Analog data about the measured small current or small voltage is amplified by the amplifier 12, which in turn is converted into digital data by the A/D converter 14, followed by being transmitted as a value to be inputted to the control means 20 via a signal line L14.

The digital data about the aspiration Ax transmitted to the control means 20 is confirmed by the interface 22 as to predetermined codes, a format and the like, followed by being transmitted to the comparing means 26 via the signal line L22.

The comparing means 26 compares the digital data about the aspiration Ax and the threshold value outputted from the data memory device 24 (Step S3). Then, the so-compared data is transmitted to the determining means 28 via the signal line L26.

The determining means 28 determines whether the result of measurement of the aspiration Ax of the subject 2 exceeds an affection or disease threshold value for lung cancer (Step S4). If the result of measurement thereof is found to exceed the threshold value (if the answer is found to be yes at Step S4), then the determining means 28 proceeds to Step S5. If the result of measurement thereof is found not to exceed the threshold value (if the answer is found to be no at Step S4), then the determining means 28 proceeds to Step S6.

If the result of measurement thereof is found to exceed the affection threshold value (if the answer is found to be yes at Step S4), then the determining means 28 judges that the subject 2 is ill, i.e., "the subject 2 has potential for lung cancer" and proceeds to Step S7.

If the result of measurement thereof is found not to exceed the affection threshold value (if the answer is found to be no at Step S4), then the determining means 28 determines that the subject 2 is not ill, i.e., "the subject 2 has no potential for lung cancer" and proceeds to Step S7.

The results of determination at Steps S5 and S6 are transmitted to the display unit 30 via the signal line L28 as output values of the control means 20. The result of determination at Step S5 or S6 referred to above is displayed on the display unit 30, and a hard copy thereof is made as needed.

FIGS. 3 through 6 show a second embodiment of the present invention.

In the first embodiment, when, for example, the sensor in which aniline hydroxylase is placed in the sensitivity portion is used as the sensor high in selectivity relative to aniline and/or ortho-toluidine, the corresponding sensor is often difficult to get and there exist difficulties associated with the storage of the sensor.

The second embodiment is configured so as to operate without using such a sensor (difficult to get and involving difficulty in its storage).

Incidentally, the first embodiment will not cause the problems that the sensor is difficult to get and involves difficulty in its storage, when the thin film sensor is used.

In FIG. 3 showing a system construction of the second embodiment in block form, a case or box-like body 5 for an acquisition means for collecting aspiration Ax of a subject 2 to be examined is provided with sensors 11a, 11b, 11c and 11d corresponding to plural (four in FIG. 3) measuring means that react to aniline and/or ortho-toluidine of the aspiration. The sensors 11a, 11b, 11c and 11d are connected to their corresponding amplifiers 12a, 12b, 12c and 12d by signal lines L11a, L11b, L11c and L11d.

An example in which the sensors 11a, 11b, 11c and 11d are brought into integrated form or assembled to make easy wiring and distributing measures, is illustrated in FIGS. 4 and 5. In FIGS. 4 and 5, the sensors 11a, 11b, 11c and 11d are shown as an assembled sensor 11A in which they are collected within a single flexible cylindrical body 11P. Lines extended out from the end of the assembled sensor 11A are signal lines L11a, L11b, L11c and L11d shown in FIG. 3.

Referring to FIG. 3 again, the amplifiers 12a through 12d are connected to A/D converters 14a through 14d via signal lines L12a through 12d respectively. The A/D converters 14a through 14d are connected to an interface 22A lying within a control means 20A via signal lines L14a through L14d.

The amplifiers 12a through 12d and the A/D converters 14a through 14d are respectively substantially similar to the amplifier 12 and the A/D converter 14 employed in the first embodiment.

The control means 20A comprises the interface 22A which receives digital signals outputted from the A/D converters 14a, 14b, 14c and 14d, a result-of-measurement combining or synthetic means 23, a comparing means 26A, a data memory or storage device (database) 24A and a determining means 28A. These devices are configured so as to process the digital signals.

The function of the interface 22A is substantially identical to the first embodiment except that the number of its inputs is four. The interface 22A is configured so as to correspond to output characteristics of the A/D converters 14a, 14b, 14c and 14d.

Further, the interface 22A is configured with code adaptation and other functions in such a manner that the digital signals outputted from the A/D converter 14 can be processed by the control means 20A. The interface 22A is connected to the result-of-measurement synthetic means 23 by a multiple signal line L22A.

As illustrated in FIGS. 6(a) and 6(b), the result-of-measurement synthetic means 23 sets axial lines radially extended in arbitrary directions with the origin as the center on the same plane by the number of sensors (sets four axial lines in the example shown in the figure) and associates the respective axial lines with the sensors in a 1:1 relationship arbitrarily.

Next, the results of measurement by the respective sensors are plotted on the axial lines associated with the sensors. The result-of-measurement synthetic means 23 is configured so as to make a decision as to whether aniline and/or ortho-toluidine exists, according to graphic forms (radar charts) defined by the plural plots. And the result-of-measurement synthetic means 23 is connected in such a manner that the result of determination is transmitted to the comparing means 26A via a signal line L23.

The data memory device 24A stores therein a large amount of data (data indicated in the radar charts by the plural sensors) about past subjects and holds threshold criteria indicative of patterns of radar charts for comparing the potentiality of lung cancer. The data memory device 24A is connected to the comparing means 26A by a signal line L24A.

Now, each of the threshold criteria referred to above is determined depending upon the sex, age, height and weight of a subject, a past history thereof and other various physical conditions. The threshold criterion is not necessarily limited to a single numeric value. Such threshold determination elements are decided by the accumulation of diagnostic data.

The comparing means 26A has the function of comparing radar charts detected by the sensors 11a, 11b, 11c and 11d from the aspiration Ax of the subject 2 and created by the result-of-measurement synthetic means 23 with the past radar charts (radar charts corresponding to threshold values) stored in the data memory device 24A. And the comparing means 26A is connected to the determining means 28A by a signal line L26A.

The determining means 28A has the function of receiving the result of comparison by the comparing means 26A and determining the potentiality of affliction with lung cancer from the aspiration Ax of the subject 2. When, for example, aniline and/or ortho-toluidine exists in the aspiration Ax over a predetermined amount, a graphic form displayed on each radar chart shows the same tendency.

Thus, if the results detected by the plural sensors are displayed on the radar charts and it is determined whether the displayed graphic forms show the same trend as the radar charts (past radar charts stored in the memory device 24A: threshold criteria) of the aspiration containing aniline and/or ortho-toluidine, then the determining means 28A can determine the existence of aniline and/or ortho-toluidine.

When the created radar charts are compared with the past radar charts stored in the memory device 24A, similarities defined as graphic forms are analogous over a predetermined reference or criterion, and an aniline and/or ortho-toluidine content in the aspiration Ax of the subject 2 is high, the determining means 28A is configured so as to determine that "the potentiality of lung cancer is high". The result of determination thereby is transmitted to the display unit 30A via a signal line L28A.

Here, when it is determined whether the graphic forms displayed on the radar charts show the same tendency as the past radar charts (threshold criteria) stored in the memory device 24A (the graphic forms indicate the same trend as the result of measurement of the aspiration containing aniline and/or ortho-toluidine), for example, a pattern recognition technique can be used. Alternatively, such determination can be made even by comparing the characteristics of the individual graphic forms one by one.

Operations of the second embodiment having the above system construction will be explained with reference to even a flowchart shown in FIG. 6.

In FIG. 6, aspiration Ax of the subject 2 is first collected by the box-like collection means 5 (Step S11).

Next, the aspiration Ax is measured by the plural sensors 11a, 11b, 11c and 11d that react to aniline (Step S12).

Analog data about small currents or small voltages measured by the plural sensors 11a, 11b, 11c and 11d are respectively amplified by the amplifiers 12a, 12b, 12c and 12d, which in turn are converted into digital data by the A/D converters 14a, 14b, 14c and 14d, followed by being transmitted as values to be inputted to the control means 20A via the signal lines L14a through L14d. The result-of-measurement synthetic means 23 plots the results measured by the sensors 11a, 11b, 11c and 11d on the axial lines corresponding to the sensors 11a, 11b, 11c and 11d to create radar charts (Step S13).

Referring to FIG. 6(a), for example, data of a sensor 11a(1) is plotted above the vertical axis of the axes orthogonal to each other, and data of a sensor 11c(3) is plotted therebelow. Further, for example, data of a sensor 11b(2) is plotted rightwardly of the horizontal axis of the orthogonal axes, and data of a sensor 11d(4) is plotted leftwardly thereof (Step S13). A graphic form obtained by connecting the plots by straight lines corresponds to a radar chart A indicated by a solid line of FIG. 6(a). This chart is transmitted to the comparing means 26A.

The comparing means 26A compares the radar chart and a radar chart B of aspiration containing aniline and/or ortho-toluidine, which is received from the data memory device 24A (Step S14).

The determining means 28A determines, using, for example, the pattern recognition technique, whether the radar chart indicative of the result of measurement of the aspiration Ax of the subject 2 is similar to a radar chart indicative of the existence of potentiality of affliction with lung cancer as the graphic form (Step S15).

If it is determined that aniline and/or ortho-toluidine exists in the aspiration Ax (if the answer is found to be yes at Step S15), then the determining means 28A proceeds to Step S16. If it is determined that no aniline and/or ortho-toluidine exists in the aspiration Ax (if the answer is found to be no at Step S15), then the determining means 28A proceeds to Step S17.

If aniline and/or ortho-toluidine exists in the aspiration Ax (if the answer is found to be yes at Step S15), then the determining means 28A determines at Step S16 that the subject 2 is being affected, i.e., "the potentiality of lung cancer exists" and proceeds to Step S18.

If no aniline and/or ortho-toluidine exists in the aspiration Ax (if the answer is found to be no at Step S15), then the determining means 28A determines at Step S17 that the subject 2 is not suffered therefrom, i.e., "the potentiality of lung cancer is absent" and proceeds to Step S18.

The determining means 28A transmits the result of determination at Step S16 or S17 to the display unit 30 via the signal line L28A as an output value of the control means 20A. The result of determination at Step S16 or S17 is displayed on the display unit 30A (Step S18) and a hardcopy thereof is made as needed.

FIGS. 7 through 12 show a third embodiment of the present invention. The third embodiment is a diagnostic system using the Internet.

In such a diagnostic system, for example, data of sensors, codes (at which the names and the like are not described for emphasis on privacy) and other information are transmitted to the center analysis center via the Internet to determine the potentiality of affliction. Thus, it is of a diagnostic system that makes the subsequent processing best.

The present system is suitable for diagnosis of solitary old people living in isolated islands, medically underserved villages and cities and can be expected to provide a welfare contribution.

In FIG. 7 showing the system construction of the third embodiment in block form with the subject side as a main body, a box-like body 5 corresponding to a collection means for collecting aspiration Ax of a subject 2 is provided with a plurality of sensors 11a, 11b, 11c and 11d (measuring means) that react to aniline and/or ortho-toluidine contained in the aspiration. The box-like body 5 is connected to its corresponding amplifier 12a by a signal line L11a, for example.

The amplifier 12a is connected to its corresponding A/D converter 14a by a signal line L12a. The A/D converter 14a is connected to a diagnostic data creating means 25 by a signal line L14a.

Paths that extend from the sensors 11b, 11c and 11d to the diagnostic data creating means 25 are similar to a path that extends from the sensor 11a to the diagnostic data creating means 25.

The diagnostic data creating means 25 has the function of creating data which pass through the A/D converters 14a, 14b, 14c and 14d from the sensors 11a, 11b, 11c and 11d and are analyzable and diagnosable by a central analysis center 50 located in a remote place. Further, the diagnostic data creating means 25 has the function of attaching personal information such as an identification number of the subject 2, etc. to the above data. And the diagnostic data creating means 25 is connected to a diagnostic data sending or transmitting means 30 by a signal line L25.

The diagnostic data transmitting means 30 may be an Internet terminal of a personal computer or the like, for example and has the function of being capable of transmitting data to an information network 40 through a signal line L30.

The information network 40 may be a general-purpose one using a normal provider or one for a restrictive area such as a LAN. The information network 40 is connected to the central analysis center 50 via a signal line L40.

The above shows the construction of an information transfer path that extends from the subject 2 side to the central analysis center 50 side.

On the other hand, the construction of an information transfer path extending from the central analysis center 50 side to the subject 2 side is as follows:

The central analysis center 50 is connected to the information network 40 by a signal line L50. The information network 40 is connected to a diagnostic result receiving means 32 placed in the same location as the diagnostic data transmitting means 40 by a signal line L41. The diagnostic result receiving means 32 is connected to the subject 2 side by a signal line L32.

The collection means 5 extends to a case 35 placed on a trucking or transport equipment Tr via a line L5 (physical distribution line). The transport equipment Tr moves to the central analysis center 50 through a transport route R such as an airway or a road. The above-described information transfer means is constituted of lines for signal transfer, whereas the paths constituted by the line L5 and the transport route R are physical routes, i.e., physical distribution lines which transport the aspiration Ax.

FIGS. 12(1) and 12(2) respectively show states in which five samples of the aspiration Ax in the carrying cases 35 are being held therein. The samples Dg shown in FIG. 12(2) are checking dummies.

Upon measurement of the collected aspiration by the four sensors, for example, five samples are prepared for a single subject 2 and all the five samples are measured by the sensors. This is because as compared with a case in which only a single sample relative to one subject is measured by the corresponding sensor, a more accurate measurement can be expected.

Here, the five samples collected from the one subject are stored in the storage case 35. The storage case 35 is marked with an identification code (e.g., barcode) 38 associated with the subject 2 from which the samples are collected.

Upon creation of diagnostic data, the individual samples stored in the same storage case 35 are measured by the sensors to obtain the results of sensor-based measurements. Thereafter, the identification code 38 is read by, for example, a barcode reader, and data about the results of sensor-based measurements and data about the identification code 38 are synthesized together.

If the diagnostic data are created in this way, then the individual corresponding to the subject 2 cannot be specified even in case of data leakage, hacking and the like. Therefore, the corresponding data make no sense as personal data.

Incidentally, the correspondence between the identification code 38 and the individual is made only when the result of diagnosis from the central processing center is sent back.

FIG. 8 is a block construction showing the central analysis center 50 of FIG. 7 illustrative of the system construction of the third embodiment as a main body.

The subject 2 and the information network 40 are connected to each other by the signal line L30 corresponding to an outward path (information transfer path from the subject 2 side to the central analysis center 50 side) and the signal line L32 corresponding to a return path (information transfer path from the central analysis center 50 to side to the subject 2 side). The information network 40 and the central analysis center 50 are connected to each other by the signal line L40 corresponding to an outward path and the signal line L50 corresponding to a return path.

The central analysis center 50 will be explained below.

In FIG. 8, the central analysis center 50 is represented as control means constituted of a digital circuit.

The central analysis center 50 comprises an interface 22C which receives digital signals from the corresponding A/D converters 14a, 14b, 14c and 14d, a result-of-measurement combining or synthetic means 23B, a comparing means 26B, a data storage or memory device (database) 24B, a determining means 28B, a diagnostic result sending or transmitting means 29B and a reexamination or reinspection unit 48. These devices are configured so as to process digital data signals except for part of the reexamination unit and output digital data.

The function of the interface 22C is substantially identical to the first embodiment except that the number of inputs is four. The functions of the details of the interface 22C in this case are not identical to the first embodiment and are configured so as to correspond to output characteristics of the respective A/D converters 14a, 14b, 14c and 14d.

Further, the interface 22C is configured with code adaptation and other functions in such a manner that the digital signals outputted from the A/D converters 14a . . . can be processed by the central processing center 50. The interface 22C is connected to the result-of-measurement synthetic means 23B by a multiple signal line L22C.

The result-of-measurement synthetic means 23B creates such radar charts as described in the second embodiment and is connected so as to transmit the result of creation to the comparing means 26B by a signal line L23B.

The data memory device (database) 24B has the function of storing a large amount of past data (radar chart-like data obtained by the plural sensors) about subjects and holding threshold values, i.e., threshold criteria at pattern recognition where the potentiality of lung cancer exists, i.e., aspiration contains aniline and/or ortho-toluidine, and transmitting the same as needed. And the data memory device 24B is connected to the comparing means 26B by a signal line L24B.

Now, each of the threshold criteria referred to above is determined case by case depending upon the sex, age, height and weight of a subject, a past history thereof and other various physical conditions. The threshold criterion is not necessarily limited to a single numeric value. Such threshold determination criteria are decided by the accumulation of diagnostic data.

The comparing means 26B has the function of comparing radar charts detected by the result-of-measurement synthetic means 23B with the past radar charts stored in the data memory device 24B. And the comparing means 26B is connected to the determining means 28B by a signal line L26B.

The determining means 28B has the function of receiving the result of comparison by the comparing means 26B and determining the potentiality of lung cancer from the aspiration Ax of the subject 2. If, for example, aniline and/or ortho-toluidine exists in the aspiration Ax over a predetermined amount, then the determining means 28B is configured so as to determine whether a graphic form displayed on each radar chart shows the same tendency and indicate the same trend as the result of measurement of the aspiration containing aniline and/or ortho-toluidine.

And the determining means 28B is connected to the diagnostic result transmitting means 29B by a signal line L26B.

The respective means lying in the central processing center 50 are substantially similar to the respective means of the second embodiment.

The diagnostic result transmitting means 29B is configured so as to transmit the result obtained by the determining means 29B to the subject 2 side via the information network 40. The diagnostic result transmitting means 29B is connected to the information network 40 by the signal line L50. Further, the diagnostic result transmitting means 29B is connected to the reexamination unit 48 by a signal line L29B.

The reexamination unit 48 has the function of analyzing the aspiration Ax by, for example, gaschromatography good in diagnosis accuracy or a large number of sensors and is configured so as to analyze raw aspiration Ax of each carried subject and take into consideration even information sent from the diagnostic result transmitting means 29B.

A route for carrying or transporting samples is configured by the line L5 and route R as described above by reference to FIG. 7.

Operations of the second embodiment having the above system construction will be explained with reference to flowcharts shown in FIGS. 9 through 11.

In the FIG. 9 showing the main control flowchart, aspiration Ax of a subject 2 is first collected by the box-like collection means 5 (Step S21).

Here, in order to take into consideration variations in aspiration Ax and improve the reliability of diagnosis, the diagnostic data creating means 25 collects the aspiration Ax as to the same subject 2 plural times as indicated by the sub flowchart of FIG. 10 (Step S41).

Further, the identification code 38 inherent in the subject 2, e.g., barcode for keeping secret the name of the subject 2 is attached as shown in FIGS. 12(1) and 12(2) in which the five sample data Sg or samples are brought together.

Now, the diagnostic data are data indicative of health conditions of individuals and data extremely high in demand for stealthiness. Thus, when the diagnostic data is created, only the identification code (refer to FIG. 12) placed in a 1:1 correspondence with each subject is attached thereto without attaching the name of the subject thereto to create the diagnostic data.

Here, five samples collected from one subject are stored in, for example, a storage case. The storage case is marked with an identification code (e.g., barcode) corresponding to the subject from which the samples are collected.

Upon creating the diagnostic data, the individual samples stored in the same storage case are measured by the sensors to obtain the results of sensor-based measurements. Thereafter, the identification code is read by, for example, a barcode reader or the like, and data about the results of sensor-based measurements and data about the identification code are synthesized together.

In order to verify or inspect the reliability of diagnosis by the central processing center 50, dummy data about an inert gas Dg such as nitrogen gas is mixed into each sample data Sg as shown in FIG. 12(2) (Step S42). A method for mixing the dummy data is performed by using such a random method that the reception side cannot recognize the samples.

When the result of diagnosis that each dummy contains aniline and/or ortho-toluidine which should not exist in the dummy, is made to the dummy, confusing between the collected samples, the mistake of handling detected signal data, etc. are judged to have occurred at the stage of processing by inspection activities or inspection personnel. Further, it can be judged that there are doubts about the diagnosis itself.

The diagnostic data are created in this way (Steps S23 and S43).

Referring to FIG. 9 again, the diagnostic data transmitting means 30 transmits the diagnostic data to the central analysis center or the central processing center 50 via the information network 40 (Step S24).

Control subsequent to Step S24 in FIG. 9 will be explained below with reference to even the construction block diagram of FIG. 8.

The central processing center 50 receives diagnostic data sent from the diagnostic data transmitting means 30 at the interface 22C and transmits the same to the result-of-measurement synthetic means 23B. The result-of-measurement synthetic means 23B creates radar charts according to data obtained by the corresponding sensors 1 through 4 (Step S25 in FIG. 9).

Then, the comparing means 26B compares each radar chart referred to above and each known radar chart stored in the data memory device 24B, i.e., the radar chart at which aniline and/or ortho-toluidine exists (Step S26). The comparing means 26B transmits the result of comparison to the determining means 28B.

The determining means 28B determines based on the above compared data whether aniline and/or ortho-toluidine indicative of the affected state of lung cancer exists in aspiration Ax (Step S27).

When it is found that aniline and/or ortho-toluidine exists (when the answer is found to be yes at Step S27), the determining means 28B proceeds to Step S31. When it is found that no aniline and/or ortho-toluidine exists (when the answer is found to be no at Step S27), the determining means 28B proceeds to Step S28.

When no aniline and/or ortho-toluidine exists (when the answer is found to be no at Step S27), the determining means 28B determines at Step S28 that "there is no potentiality of lung cancer". The result of diagnosis thereof is transmitted by the diagnostic result transmitting means 29B via the information network (Internet) 40 (Step S29). Then, the diagnostic result transmitting means 29B notifies the result of diagnosis to the corresponding subject 2 with which the identification code 38 coincides (Step S30).

The result of diagnosis is checked as shown in the flowchart of FIG. 11 with respect to the notification of the result of diagnosis at Step S30. That is, the result of diagnosis is received (Step S51 in FIG. 11), the result of diagnosis relative to the inert gas such as nitrogen gas transmitted by each dummy is checked (Step S52), and the reliability of diagnosis is determined (Step S52).

When aniline and/or ortho-toluidine exists in FIG. 9 again (when the answer is found to be yes at Step S27), the determining means determines at Step S31 that there is a need for reexamination. It is necessary to, with aspiration itself collected with respect to the subject (corresponding to a subject high in the potentiality that aniline and/or ortho-toluidine will be contained, in other words, a subject high in the potentiality of lung cancer) as a sample, analyze the sample per se by a technique such as gaschromatography without using electronic data and make a decision higher in accuracy. Therefore, the diagnostic result transmitting means 29B transmits a request for transmission of each sample (raw aspiration) of the aspiration Ax of the corresponding subject 2 by way of the information network (Internet) 40 (Step S32).

On the subject side having accepted the demand for the transmission of each sample (raw aspiration) of the aspiration Ax via the diagnostic result receiving means 32 (FIG. 7), the aspiration sample Sg is transported from the central processing center 50 to the reexamination unit 48 of the central processing center 50 by a transport means Tr (FIG. 8) in the form shown in FIG. 12(1) or 12(2) (Step S33 in FIG. 9).

At this time, an inert gas is mixed into plural samples as each dummy during aspiration sampling in a manner similar to the execution at Step S42 in FIG. 10 and used to confirm the reliability of reexamination.

The reexamination unit 48 inspects the aspiration samples by gaschromatography or a wide variety of sensors (eight types in the figure) (Step S34) and notifies each of the results of inspection to the corresponding subject 2 to which the identification code 38 coincides, as the result of diagnosis via the information network (Internet) 40 (Step S35).

Operative effects at the time that the number of samples is increased upon inspection at the reexamination unit 48, will be explained with reference to FIG. 13.

A procedure for detecting aspiration in a collection device 5 by eight sensors 11a, . . . , amplifying their results of detection by an amplifier 12C, converting the same into digital data by an A/D converter 14C and transmitting the digital data to a result-of-measurement combining or synthetic means 23C is substantially identical to the second embodiment except that the number of samples is increased to eight equivalent to twice the above number A procedure for allowing a comparing means 26B to compare each radar chart created by the result-of-measurement synthetic means 23C and the past affection data stored in a memory device 24C is also substantially identical to the second embodiment.

The result-of-measurement synthetic means 23C creates the results of detection by the eight sensors as a radar chart RC1 shown in FIG. 13(1). An affection radar chart RC2 shown in FIG. 13(2) is taken or pulled out from the memory device 24C. In the two data charts RC1 and RC2, values that get across axes 1, 2, 3 and 4 are identical to one another. When they are judged by only the values that cross the axes 1, 2, 3 and 4, they are judged to be the same data. In other words, the radar chart RC1 is judged to be identical to the affection radar chart RC2 indicative of affliction with lung cancer. The subject is diagnosed as being afflicted with the lung cancer.

In FIG. 13(3), values that cross axes 5, 6, 7 and 8 are completely different from one another in radar charts RC1 and RC2.

Thus, if a decision is made based on the results of detection by the eight sensors, then the radar chart RC1 is judged to differ from the affection radar chart RC2 indicative of the subject being afflicted with lung cancer. Thus, the subject is not diagnosed as being affected by the lung cancer.

Thus, it is possible to make a higher accuracy diagnosis as the number of sensors increases. Therefore, a misdiagnosis can be prevented from occurring.

A fourth embodiment of the present invention will next be explained with reference to FIGS. 14 through 16.

While the third embodiment has used the sensor constructed by combining the plural sensors, the fourth embodiment shown in FIGS. 14 through 16 makes use of a sensor (sensor that reacts with an indicated substance (e.g., aniline, ortho-toluidine or the like) in a so-called 1:1 relationship) that reacts with only odors indicative of lung cancer and other diseases to be detected or the indicated substance. In the fourth embodiment, a thin film sensor is used as such a sensor.

Such a thin film sensor is preferably constructed to be capable of being used even in the air (within a vapor phase environment: e.g. during aspiration) and in the liquid (within a liquid phase environment: e.g., in body fluid, urine or the like).

The fourth embodiment is equipped with a construction schematically similar to the third embodiment and constructed as a diagnostic system using the Internet.

In FIG. 14 showing the subject side with the system construction of the fourth embodiment as a main body in block form, a box-like body 501 corresponding to an acquisition or collection means for collecting aspiration Ax-1 of a subject 2 is provided with a thin film sensor 11a1 (measuring means) that reacts with only aniline and/or ortho-toluidine contained in the aspiration Ax-1.

Here, aniline and/or ortho-toluidine is an indicated substance indicative of the existence of lung cancer.

The sensor 11a1 is connected to an amplifier 12a1 by a signal line L11a.

Incidentally, a substance, i.e., a specimen intended for collection in the box-like body 501 corresponding to the collection means is not limited to the aspiration Ax-1 of the subject 2 but may be sweat, spit or urine or the like.

The amplifier 12a1 is connected to an A/D converter 14a1 by a signal line L12a1. The A/D converter 14a1 is connected to a diagnostic or diagnosis data creating means 251 by a signal line L14a1.

A signal line L01 for transmitting personal information such as an identification number of a subject 201 is connected to the diagnosis data creating means 251.

The diagnosis data creating means 251 has the function of creating analyzable and diagnosable diagnosis data in conjunction with data having passed through the amplifier 12a1 and the A/D converter 14a1 from the sensor 11a1 and the personal information of the subject 201.

The diagnosis data creating means 251 is connected to a diagnosis data transmitting means 301 by a signal line L251.

The diagnosis data transmitting means 30 is an Internet terminal of a personal computer or the like. Further, the diagnosis data transmitting means 30 has the function of being capable of transmitting data to an information network 401 via a signal line L301.

The information network 401 may be a general-purpose one using a normal provider or one for a restrictive area such as a LAN.

The information network 401 is connected to a central analysis center 501 via signal lines L401 and L501. The information network 401 is connected to a diagnostic result receiving means 321 by a signal line L411.

The diagnostic result receiving means 321 is connected to the subject 201 via a signal line L321.

The central analysis center 501 is connected to the subject 2 side via the signal lines L401 and L501 and the information network 401. In addition to above, however, the central analysis center 501 is connected with a channel or path route R-1, e.g., a physical distribution route such as an airway or a road through a transport equipment Tr-1 for carrying or forwarding the aspiration Ax-1.

Incidentally, the box-like body 501 corresponding to the collection means is held or accommodated in a case 351 placed on the transport equipment Tr-1 via a line L501.

FIG. 15 shows as a block diagram the construction of an overall system with the central analysis center 501 of FIG. 14 as a principal or main body.

In FIG. 15, the subject 201 and the information network 401 are connected to each other via the signal lines L301 and L321. The information network 401 and the central processing center 501 are connected to each other via the signal lines L401 and L501.

The central processing center 501 comprises an interface 22C1 which receives a digital signal from the A/D converter 14a1, a comparing means 26B1, a data storage or memory device (database) 24B1, a determining means 28B1, a diagnostic result transmitting means 29B1 and a reexamination unit 481.

These devices are configured so as to process the digital signal except for the reexamination unit 481 and outputs the digital signal.

The interface 22C1 is substantially identical to the first embodiment in function and constructed so as to adapt to the output characteristic of the A/D converter 14a1.

Further, the interface 22C1 is constructed with code adaptation and other functions in such a manner that the digital signal outputted from the A/D converter 14a1 can be processed by the central processing center 501. The interface 22C1 is connected to the comparing means 26B1 by a signal line L23B1.

The comparing means 26B1 has the function of comparing data obtained by processing the aspiration Ax-1 of the subject 2 and the past data stored in the data memory device 24B1. The comparing means 26B1 is connected to the data memory device 24B1 by a signal line L24B1.

The data memory device 24B1 has the function of storing therein a large amount of past subject data obtained by the sensor 11a1 and holding threshold values or criteria at the time that the indicated substance is contained, and transmitting the corresponding data or threshold value when necessary.

Here, the threshold value or the criterion is determined case by case depending upon the sex, age, height and weight of a subject, a past history thereof and other various physical conditions. It is not necessarily limited to a single numeric value. Such threshold determination criteria are decided by the accumulation of diagnostic data.

The determining means 28B1 has the function of receiving the result of comparison by the comparing means 26B1 and determining the potentiality of a specific disease for the subject 201. If, for example, aniline and/or ortho-toluidine exists in the aspiration Ax-1 over a predetermined amount, then the determining means 28B1 is configured so as to determine whether the subject is afflicted with lung cancer. The determining means 28B1 is connected to the diagnostic result transmitting means 29B1 by a signal line L28B1.

The construction of the central processing center 501 is almost similar to that of the third embodiment except for the construction related to the creation of radar charts.

The diagnostic result transmitting means 29B1 is constructed so as to send or transmit the result obtained by the determining means 28B1 to the subject 201 via the information network 401. The diagnostic result transmitting means 29B1 is connected to the information network 401 by a signal line L501.

Further, the diagnostic result transmitting means 29B1 is connected to the reexamination unit 481 lying in the central processing center 501 by a signal line L29B1.

The reexamination unit 481 is similar to that of the third embodiment.

Operations of the fourth embodiment having the above system construction are shown in a flowchart of FIG. 16.

Here, the flowchart of FIG. 16 is schematically similar to FIG. 9 corresponding to the flowchart indicating the operations of the third embodiment.

Different points between FIG. 16 and FIG. 9 will principally be explained below.

In FIG. 16, aspiration Ax (or sweat, human waste, urine) Ax-1 of the subject 201 is collected by the box-like body 501 (Step S121) and measured by the thin film sensor 11a1 (Step S122).

In order to keep secret the name of the subject 201 in a manner similar to the third embodiment, the diagnosis data creating means 251 creates diagnostic data using the data measured by the thin film sensor 11a1 (Step S123).

The diagnostic data is transmitted to the central processing center 501 (Step S124). The central processing center 501 compares the transmitted diagnostic data with the corresponding threshold value stored in the data memory device 24B1 (Step S126) and transmits the result of comparison to the determining means 28B1.

If, for example, a target for disease is of lung cancer, then the determining means 28B1 determines whether aniline and/or ortho-toluidine exists (Step S127). When aniline and/or ortho-toluidine exists (when the answer is found to yes), the determining means 28B1 proceeds to Step S131. When it does not exist (when the answer is found to be no), the determining means 28B1 proceeds to Step S128.

When aniline and/or ortho-toluidine does not exist, the determining means 28B1 determines at Step S128 that "there is no potentiality of lung cancer". The result of diagnosis is transmitted to the subject 201 (Step S219). The diagnostic result receiving means 321 notifies the diagnostic result to the subject 201 with which the identification code coincides (Step S130).

When it is found at Step S127 that aniline and/or ortho-toluidine exists, it is judged at Step S131 that "there is a need for reexamination with respect to the corresponding subject (corresponding to a subject high in the potentiality that aniline and/or ortho-toluidine will be contained in the aspiration, in other words, a subject high in the potentiality of lung cancer). The central processing center 501 transmits a request for transmission of a sample of aspiration Ax-1 of the corresponding subject 201 (Step S132).

The subject 201 side sends the sample of the aspiration Ax-1 to the reexamination unit 481 in accordance with the sample transmission request made from the central processing center 501 (Step S133).

The reexamination unit 481 inspects the sample of the aspiration Ax-1 by means of a high-accuracy measuring device such as gaschromatography (Step S134) and notifies the result of inspection to the subject 201 side (Step S135).

The respective embodiments shown in the figures are shown only as illustrations and by no means limited to the technical scope of the present invention.

Although, for example, each illustrated embodiment has explained that aniline or ortho-toluidine is detected as the indicated substance and the decision as to whether the corresponding subject is afflicted with lung cancer is made based on it, it is also possible to make a decision as to other disease. The indicated substance can also be selected from alkane, alkene, alkine, diene, cyclic carbon hydride, aliphatic carbon hydride, acyclic carbon hydride, arene, alcohol, ether, ketone, aldehyde, carbonyl, carbanion, polynuclear aromatic compounds, biological molecules, isoprene, isoprenoid, protein, volatile organic compounds (VOC), VOA, indole, skatole, diamine, pyridine, picoline, sulphuric compounds, halogenated compounds, fatty acid, organic acid, organic base, non-volatile gas, CO, $CO_2$, NO, $NO_2$, $NH_3$, $H_2$, S, and COS.

BRIEF DESCRIPTION OF THE DRAWINGS

FIG. 10 is a flowchart depicting operations of the third embodiment.

FIG. 11 is a flowchart showing operations of the third embodiment.

FIG. 12 is a diagram for describing the forms of samples.

EXPLANATION OF REFERENCE NUMERALS

Figure 2:
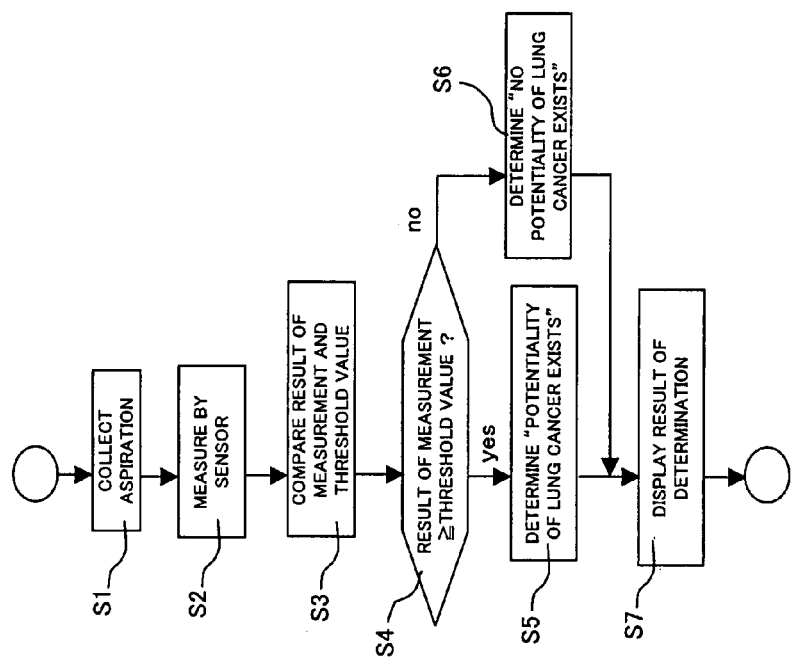
FIG. 2 is a flowchart illustrating operations of the first embodiment.
Figure 1:
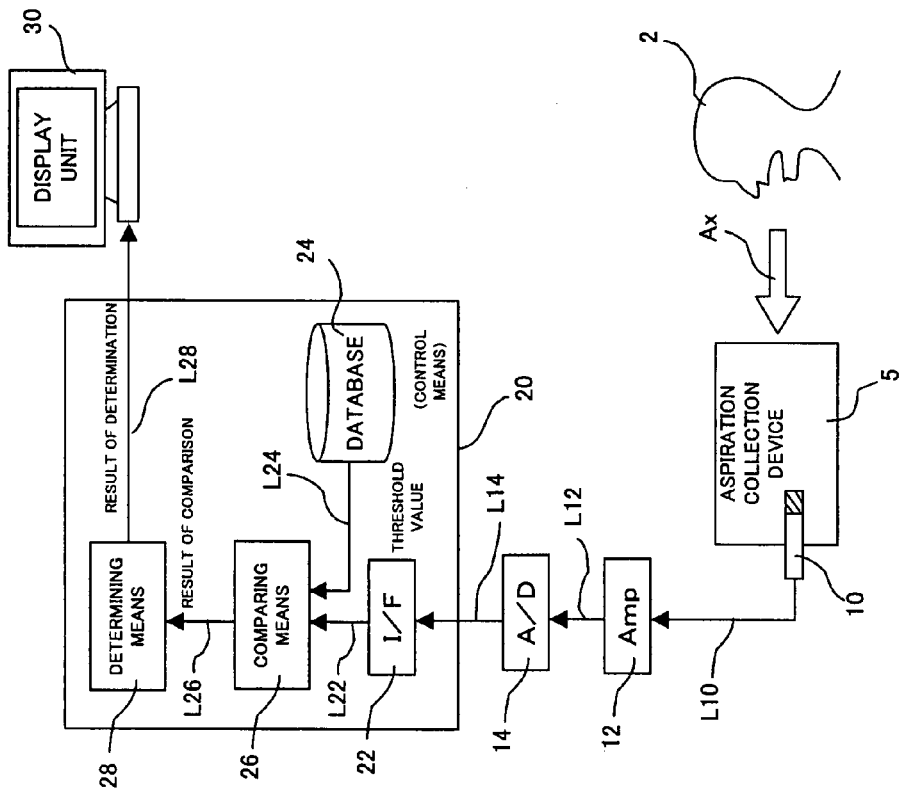
FIG. 1 is a block diagram showing an overall construction of a first embodiment of the present invention.
Figure 3:
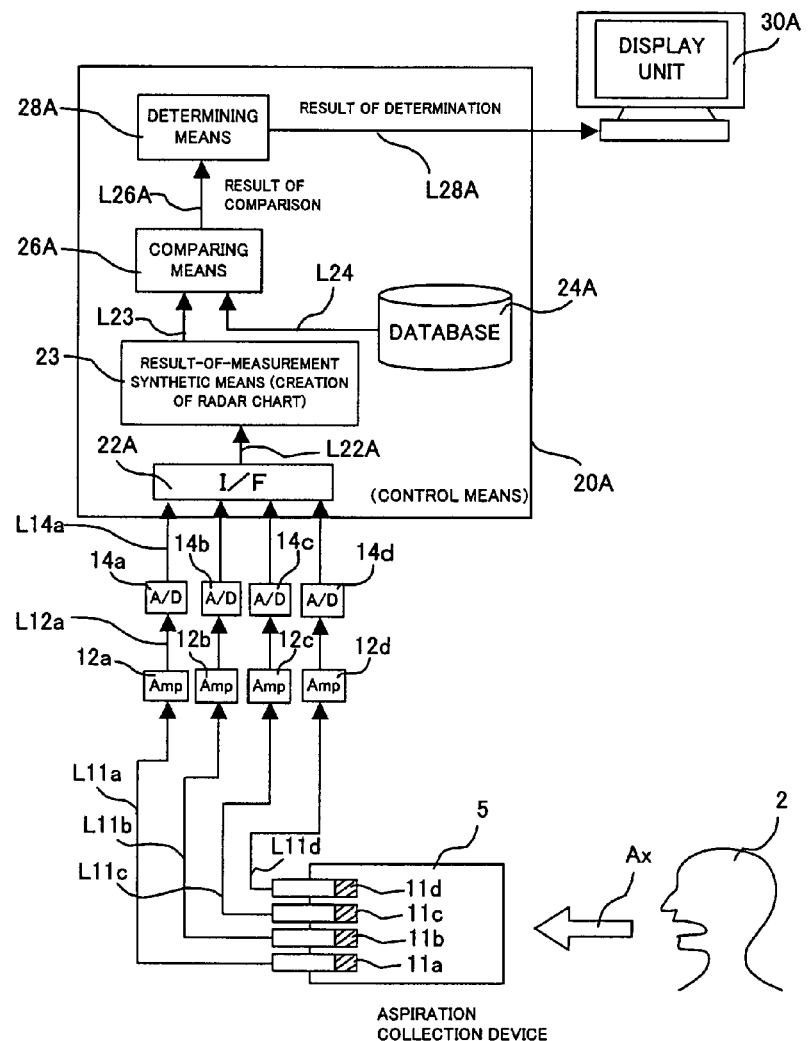
FIG. 3 is a block diagram depicting an overall construction of a second embodiment.
Figure 4:
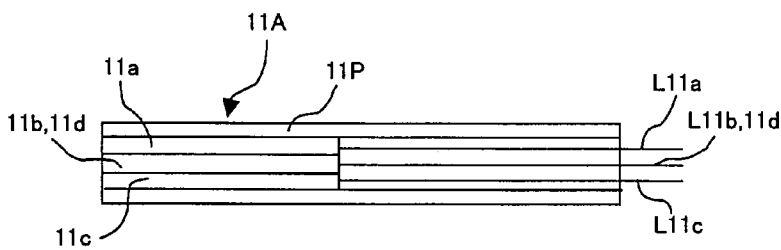
FIG. 4 is a side sectional view showing a plurality of sensors integrated into one.
Figure 5:
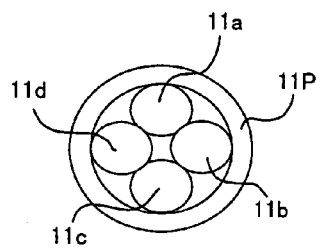
FIG. 5 is a front view showing the sensors of FIG. 4.
Figure 6:
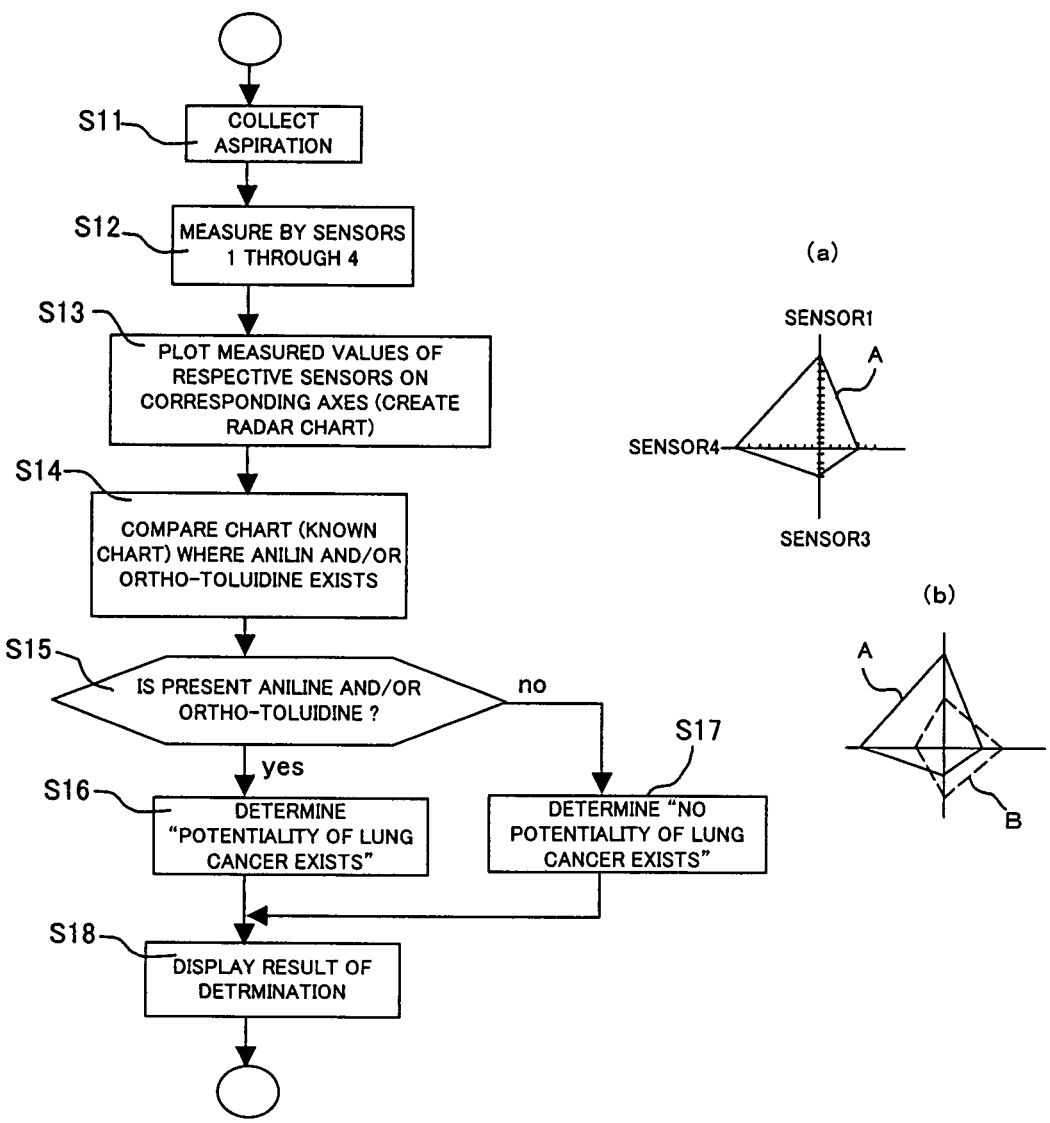
FIG. 6 is a flowchart showing operations of the second embodiment.
Figure 7:
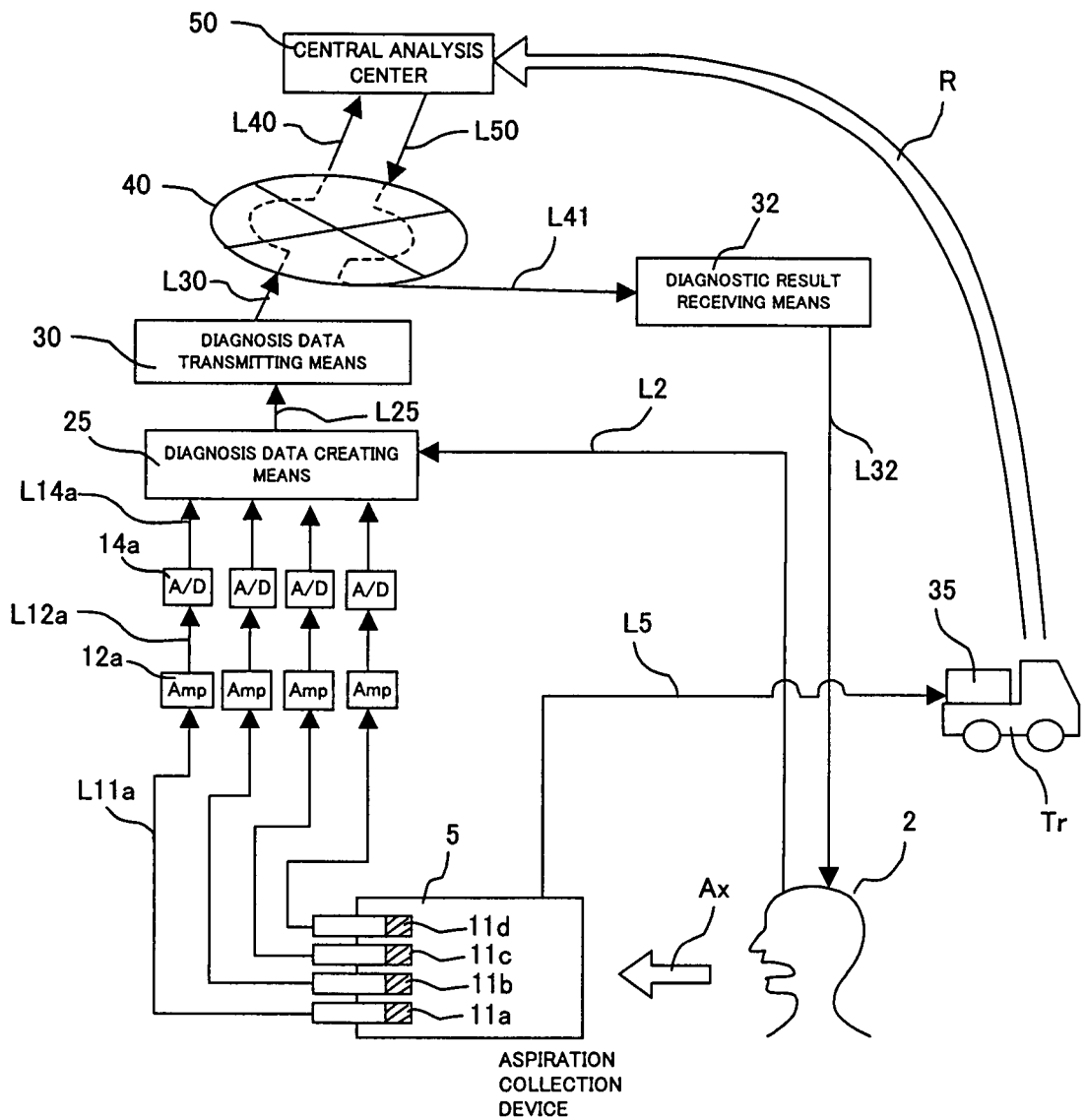
FIG. 7 is a block diagram showing an overall construction of a third embodiment with a subject side as a main body.
Figure 8:
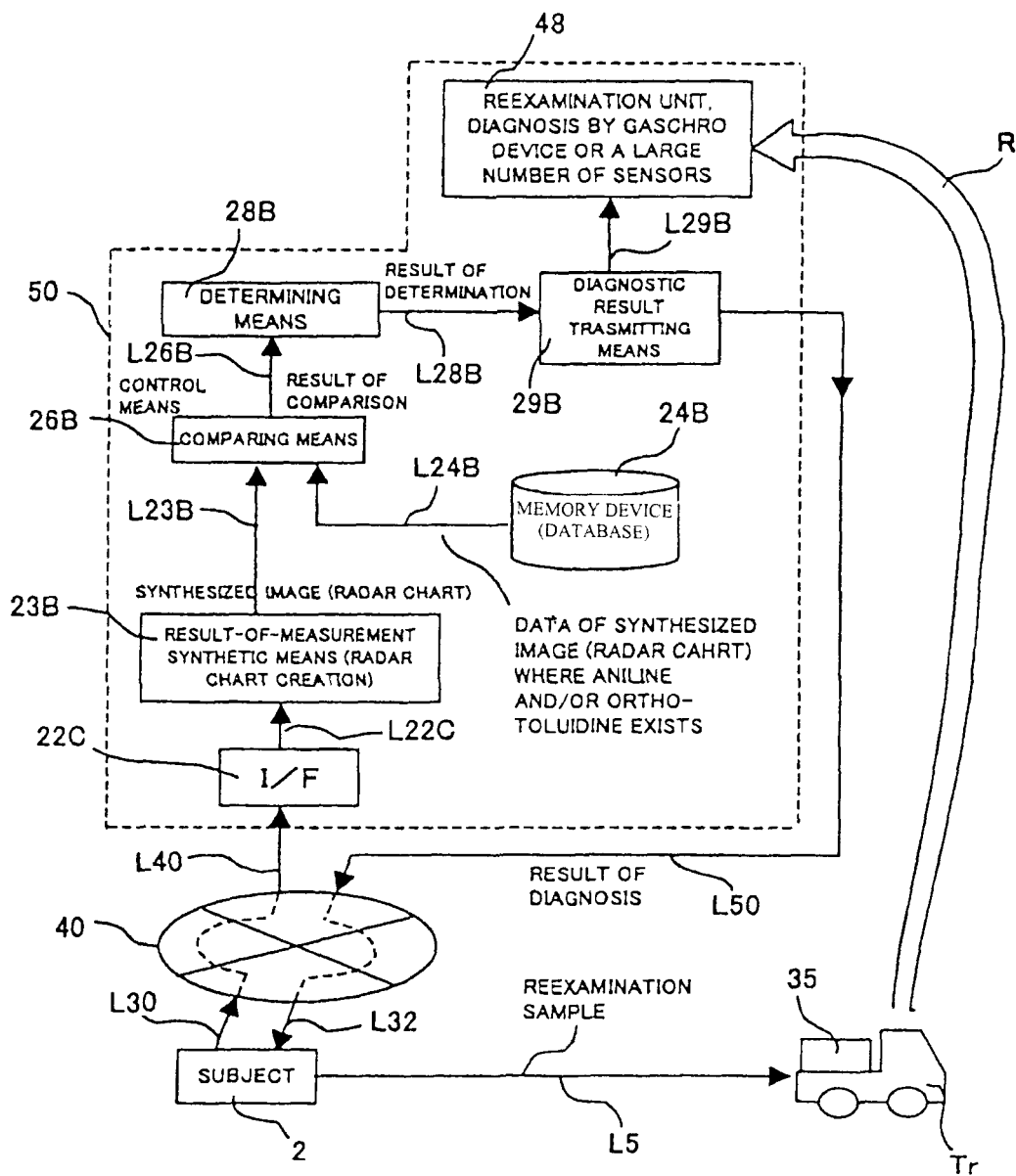
FIG. 8 is a block diagram illustrating an overall construction of the third embodiment with a central analysis center as a main body.
Figure 9:
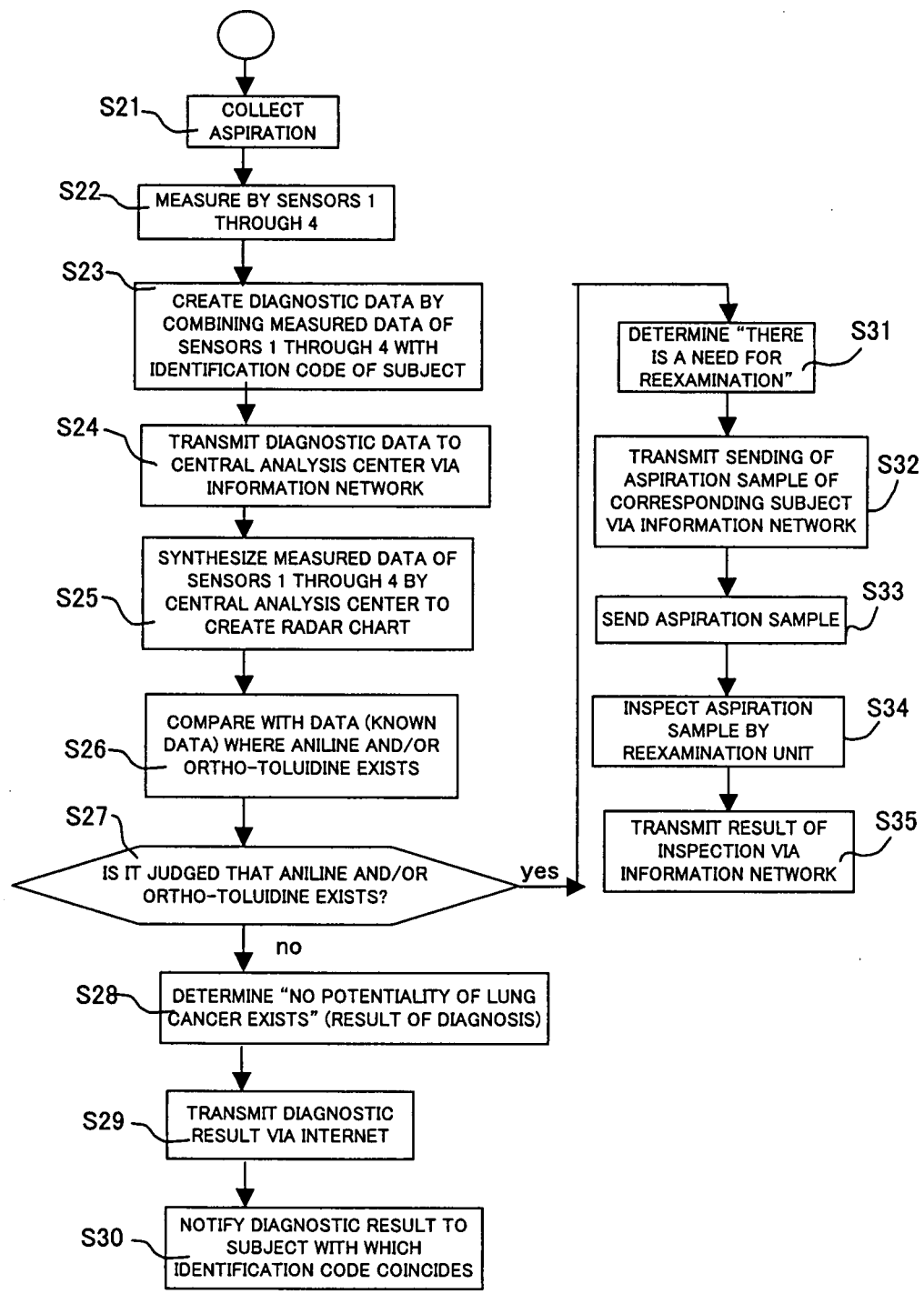
FIG. 9 is a flowchart showing operations of the third embodiments.
Figure 13:
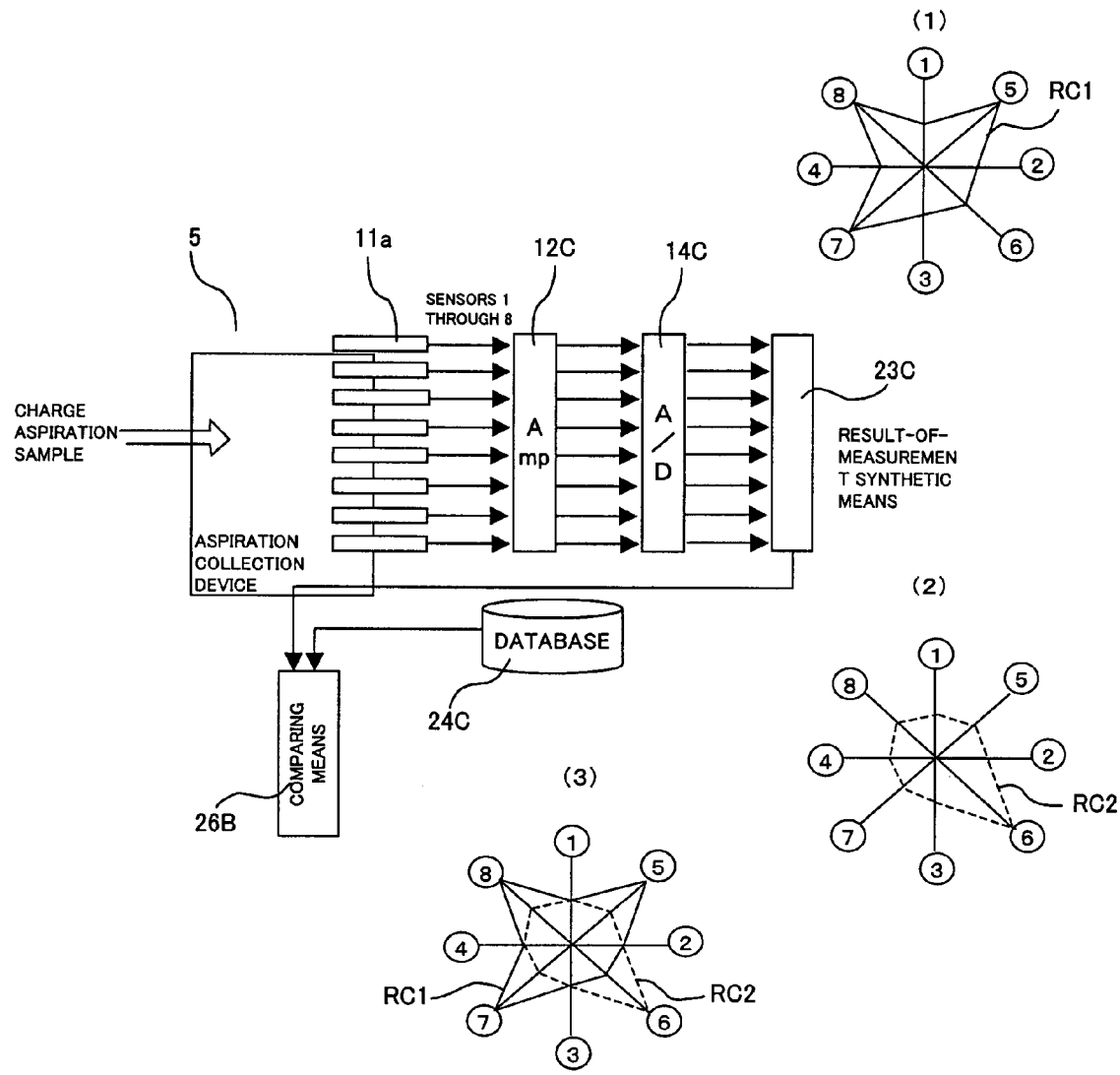
FIG. 13 is an explanatory view showing improvements in diagnostic accuracy where a large number of sensors for re-examination are provided.
Figure 14:
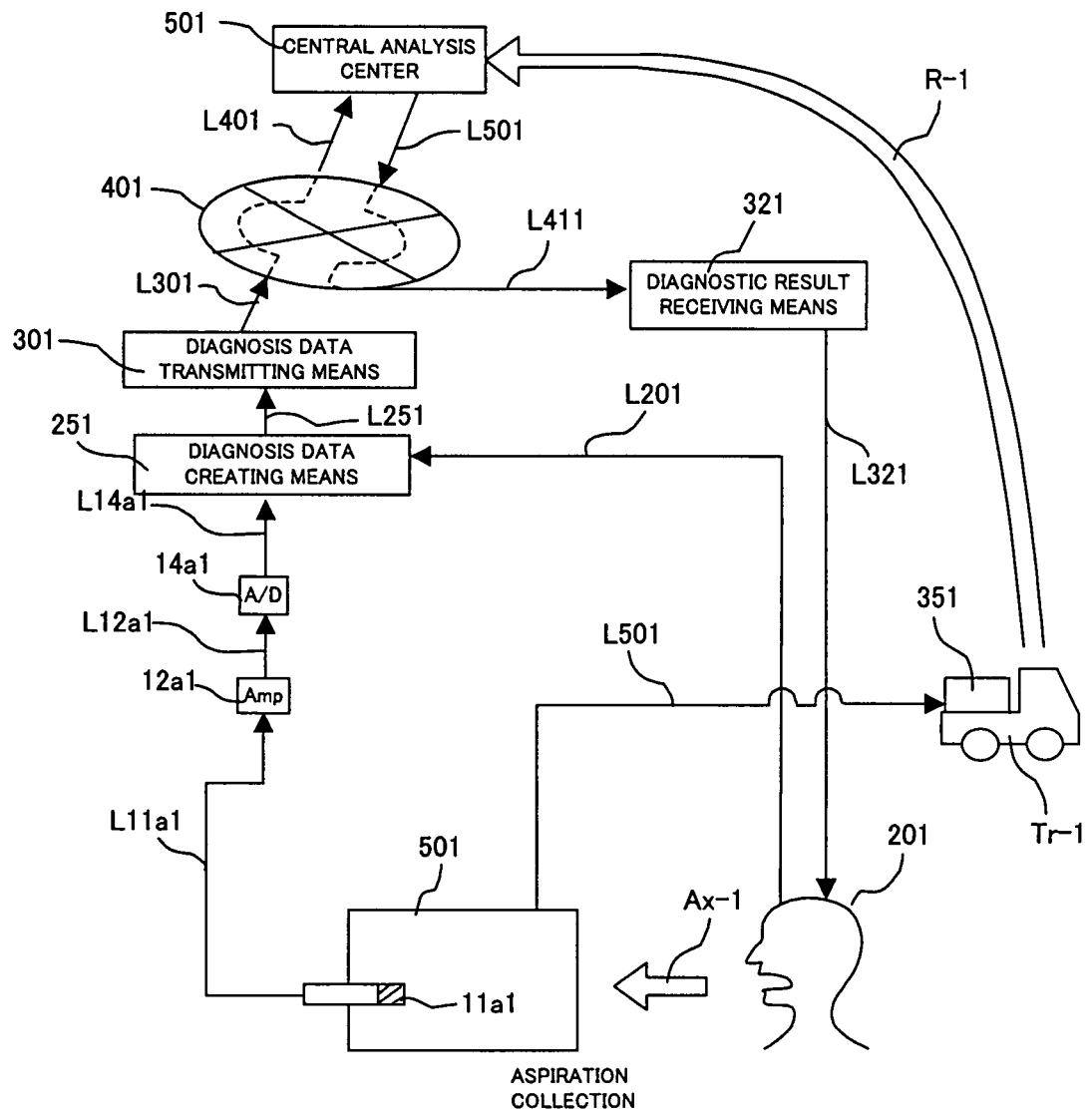
FIG. 14 is a block construction diagram illustrating an overall construction of a fourth embodiment.
Figure 15:
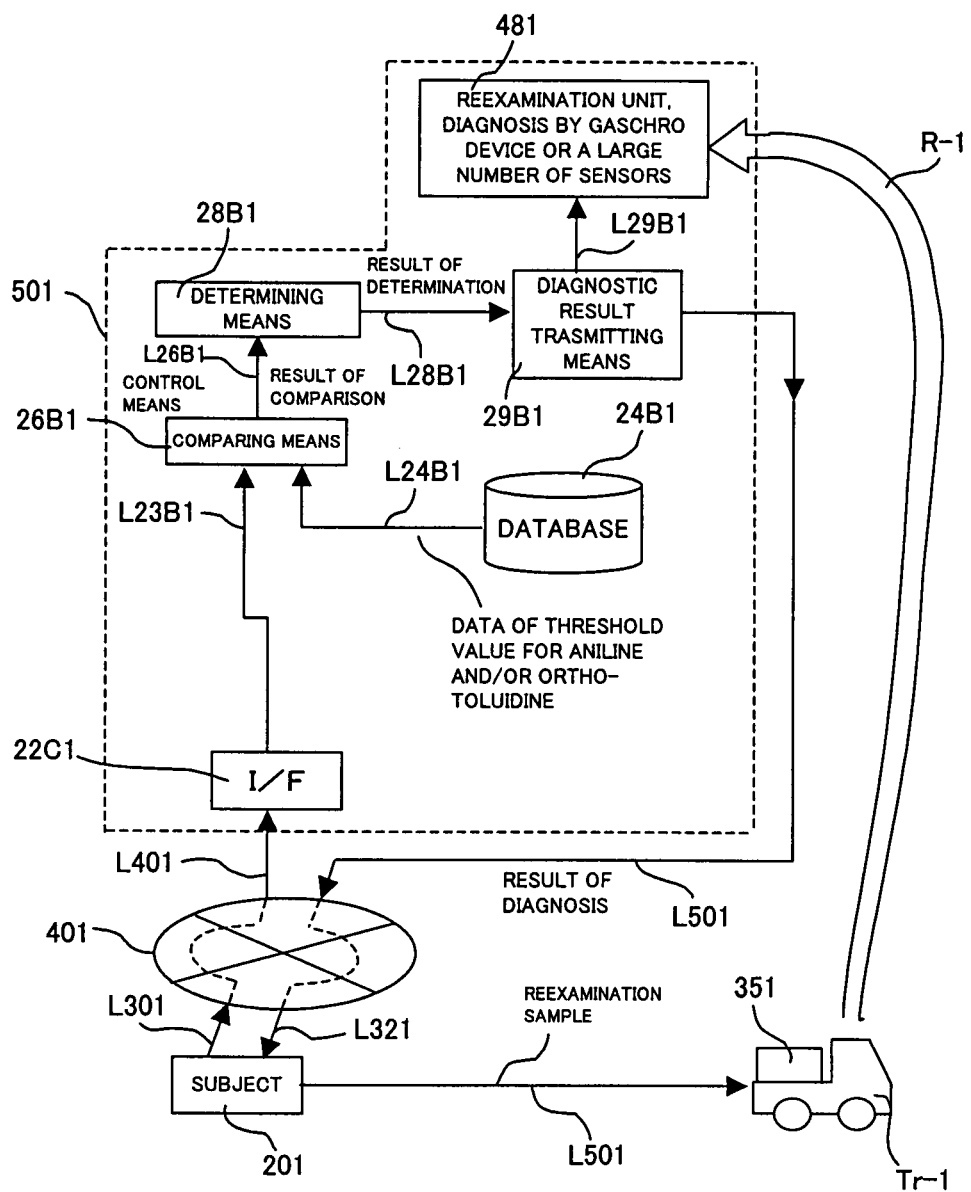
FIG. 15 is a block diagram showing the fourth embodiment with its central analysis center (control means) as a main body.
Figure 16:
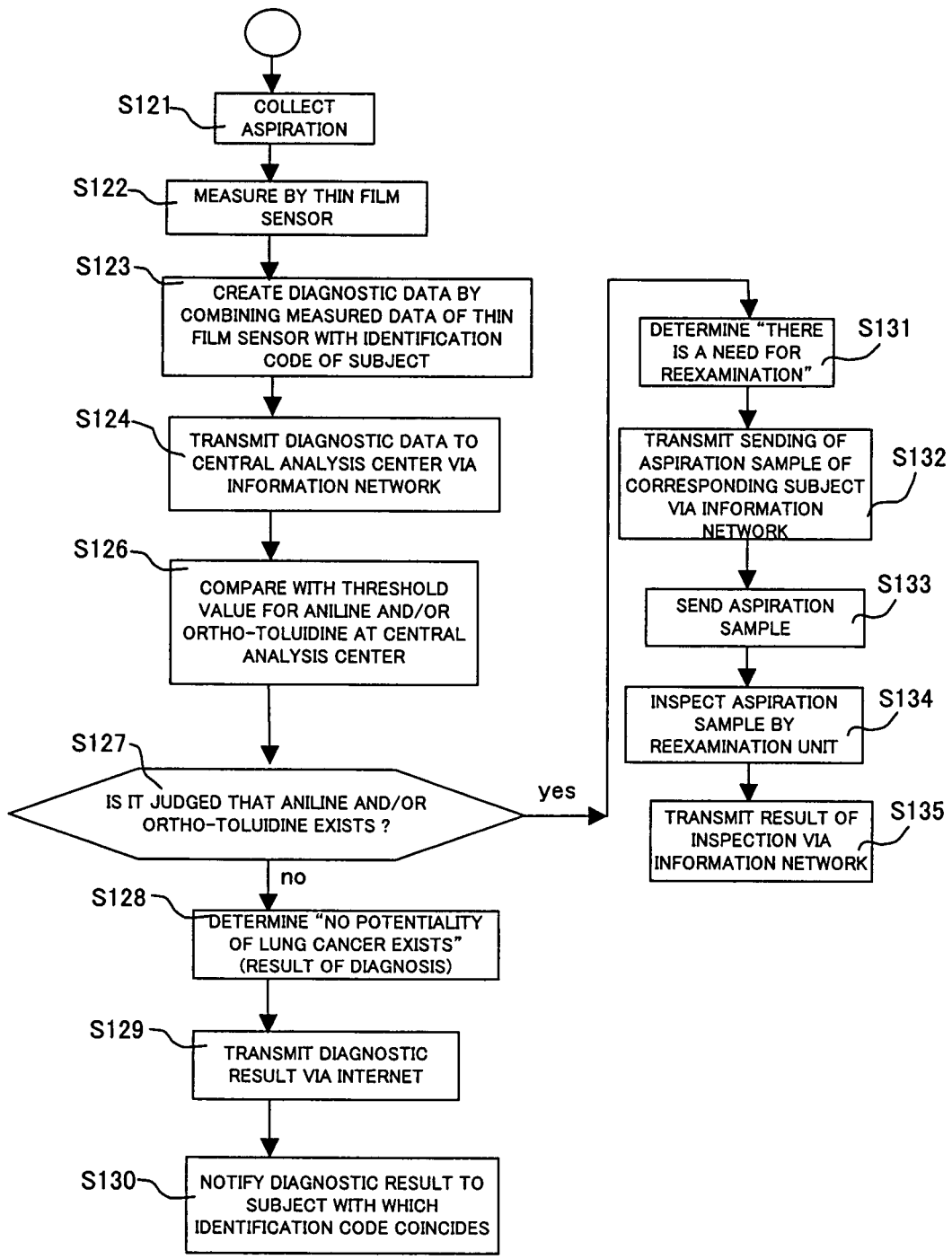
FIG. 16 is a flowchart illustrating operations of the fourth embodiment.

Ax . . . aspiration
2 . . . subject
5 . . . acquisition means, acquisition device
10, 11 . . . measuring means, sensor
12 . . . amplifier
14 . . . A/D converter
20, 20A, 50 . . . control means
22 . . . interface
24 . . . data memory device
26 . . . comparing means
28 . . . determining means
30 . . . display means
40 . . . information network

The invention claimed is:

1. A disease diagnostic system comprising:
collecting means for collecting an odor-emitting substance from a subject and storing the same therein;
a thin film sensor, for measuring whether an indicated substance indicative of the existence of a disease is contained in the odor-emitting substance stored in the collecting means, being constructed so as to sense only an indicated substance to be detected and so as to be capable of detecting a concentration of a detected target, said thin film sensor is constituted of a porous material in which a plurality of pores in a nano-level are formed, and is constructed so as to exhibit or exert selectivity necessary as a sensor by intruding molecules of a substance to be detected in the pores formed in a nano-level and so as to be capable of detecting a concentration of the detected target by transmitting an output signal in association with an amount of the detected target intruded in the pores; and
control means for processing a signal indicative of a result of measurement by the thin film sensor to thereby determine whether the subject is afflicted with the disease, wherein
a box-like body for collecting aspiration of a subject is provided with the thin film sensor, the sensor is connected to an amplifier, the amplifier is connected to an A/D converter, the A/D converter is connected to a diagnostic or diagnosis data creating means;
a signal line for transmitting personal information of the subject is connected to the diagnosis data creating means, the diagnosis data creating means has a function of creating analyzable and diagnosable diagnosis data in conjunction with data having come from the sensor and the personal information of the subject, the diagnosis data creating means is connected to a diagnosis data transmitting means;
the diagnosis data transmitting means has a function of transmitting data to an information network, the information network is connected to a central analysis center and a diagnostic result receiving means, the diagnostic result receiving means is connected to the subject;
the central analysis center is connected to the subject via the information network and by means of a transport means;
the central analysis center comprises a comparing means, a data storage or memory device, a determining means, a diagnostic result transmitting means and a reexamination unit;
the comparing means is connected to the data memory device and has a function of comparing data obtained by processing the aspiration of the subject and past data stored in the data memory device;
the data memory device has a function of storing therein a large amount of past data for the subject which data is obtained by the sensor, a function of holding threshold values or criteria in a case that the indicated substance is contained, and a function of transmitting corresponding data or threshold value when necessary;
the determining means is connected to the diagnostic result transmitting means and has a function of receiving a result of a comparison by the comparing means and a function of determining if a aniline and/or ortho-toluidine exists in the aspiration of the subject;
the diagnostic result transmitting means is connected to the reexamination unit and is constructed so as to send or transmit a result obtained by the determining means to the subject via the information network; and
the reexamination unit has a function of analyzing the aspiration carried by the transport means and a function of considering information being sent from the diagnostic result transmitting means, and when the determining means determines that aniline and/or ortho-toluidine exists in the aspiration, the reexamination unit analyzes the aspiration.

2. A disease diagnostic system comprising:
collecting means for collecting an odor-emitting substance from a subject and storing the same therein;
measuring means for measuring whether an indicated substance indicative of the existence of a disease is contained in the odor-emitting substance stored in the collecting means; and
control means for processing a signal indicative of a result of measurement by the measuring means to thereby determine whether the subject is afflicted with the disease;
the measuring means has plural types of sensors, and the control means is constructed for processing by setting coordinate axes extending radially in arbitrary directions with an origin of each coordinate axis as a center on the same plane, with the number of coordinate axes being the same number as the plural types of sensors, associating the respective coordinate axes with the plural types of sensors in a 1:1 relationship arbitrarily, for plotting the results of measurement by the measuring means on the associated coordinate axes, and for determining according to each of graphic forms defined by plural plots whether an indicated substance indicative of the presence of a disease exists;

the collecting means and the measuring means are provided in the same physical location, the control means is provided in a physical location spaced away from the collecting means and the measuring means, the collecting means and the measuring means, and the control means are connected to one another by an information network and a transport means, and a signal indicative of a result of measurement by said measuring means is transmitted to the control means via the information network;

a box-like body corresponding to the collecting means for collecting aspiration of a subject is provided with a plurality of sensors, that the sensors are constituted of a semiconductor as the measuring means, each of which sensors is connected to an amplifier, the amplifier is connected to an A/D converter, the A/D converter is connected to a diagnostic data creating means;

the diagnostic data creating means has a function of creating data which is analyzable and diagnosable by a central analysis center by signals transmitted from the sensors and a function of attaching personal information of the subject to the above-mentioned data, and is connected to a diagnostic data sending or transmitting means;

the diagnostic data transmitting means has a function of transmitting data to the information network, the information network is connected to the central analysis center;

a sample case of the transport means is constructed so as to receive the aspiration of the subject and so as to transport to the central analysis center, and receives a plurality of samples of the aspiration of the subject and a dummy sample, an identification code being associated with the subject is attached to the sample case;

the diagnostic data transmitting means synthesizes measurement results of the individual samples stored in the same storage case which results are transmitted from the sensors and the identification code together upon creation of diagnostic data;

the central analysis center comprises a result-of-measurement synthetic means, a comparing means, a data storage or memory device, a determining means, a diagnostic result sending or transmitting means and a reexamination unit;

the result-of-measurement synthetic means is constructed so as to create the graphic forms defined by plural plots and so as to transmit the graphic forms to the comparing means;

the data memory device has a function of storing a large amount of past data about the subject and a function of holding threshold values for determining whether the indicated substance is contained, is constructed so as to transmit the past data and threshold values upon being necessary, and is connected to the comparing means;

the comparing means has a function of comparing the graphic forms being created by the result-of-measurement synthetic means with past graphic forms stored in the data memory device by a pattern recognition technique, and is connected to the determining means;

the determining means has a function of receiving the result of comparison by the comparing means and a function of determining whether aniline and/or ortho-toluidine is contained in the aspiration of the subject, and is connected to the diagnostic result transmitting means;

the diagnostic result transmitting means is constructed so as to transmit the result obtained by the determining means to the subject via the information network, and is connected to the information network and the reexamination unit;

the reexamination unit has a function of analyzing the aspiration of the subject transported by the transport means and a function of considering an information being sent from the diagnostic result transmitting means, and the number of sensors of the reexamination unit is increased from that of the box-like body, and when the determining means determines that aniline and/or ortho-toluidine exists in the aspiration, the reexamination unit analyzes the aspiration.

* * * * *